(12) United States Patent
Consigny

(10) Patent No.: US 9,186,329 B2
(45) Date of Patent: *Nov. 17, 2015

(54) METHOD OF TREATING MALIGNANT SOLID TUMORS

(71) Applicant: Abbott Cardiovascular Systems Inc., Santa Clara, CA (US)

(72) Inventor: Paul M. Consigny, San Jose, CA (US)

(73) Assignee: ABBOTT CADIOVASCULAR SYSTEMS INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/749,612

(22) Filed: Jan. 24, 2013

(65) Prior Publication Data

US 2013/0129817 A1    May 23, 2013

Related U.S. Application Data

(63) Continuation of application No. 12/487,094, filed on Jun. 18, 2009, now Pat. No. 8,383,671.

(51) Int. Cl.
| | |
|---|---|
| *A61K 9/14* | (2006.01) |
| *A61K 9/127* | (2006.01) |
| *A61K 9/16* | (2006.01) |
| *A61K 31/335* | (2006.01) |

(52) U.S. Cl.
CPC ............. *A61K 9/146* (2013.01); *A61K 9/127* (2013.01); *A61K 9/1273* (2013.01); *A61K 9/14* (2013.01); *A61K 9/1629* (2013.01); *A61K 31/335* (2013.01)

(58) Field of Classification Search
CPC ......... A61K 9/14; A61K 9/127; A61K 9/146; A61K 9/1273; A61K 9/1629; A61K 31/335
See application file for complete search history.

(56) References Cited

U.S. PATENT DOCUMENTS

| 4,276,885 A * | 7/1981 | Tickner et al. ............ 424/9.52 |
| 2005/0123614 A1 | 6/2005 | Kim et al. |
| 2005/0186261 A1 | 8/2005 | Avelar et al. |
| 2006/0034925 A1 | 2/2006 | Au et al. |
| 2006/0189520 A1 | 8/2006 | Brand et al. |
| 2007/0184082 A1 | 8/2007 | Magdassi et al. |
| 2007/0207211 A1 | 9/2007 | Zeigerson |
| 2008/0039362 A1 | 2/2008 | Shebuski et al. |
| 2008/0181939 A1 | 7/2008 | Discher et al. |
| 2008/0267947 A1 | 10/2008 | Cirrito et al. |
| 2009/0297621 A1 | 12/2009 | Lim et al. |

FOREIGN PATENT DOCUMENTS

| WO | WO 2004/004644 | 1/2004 |
| WO | WO 2005/079703 | 9/2005 |

OTHER PUBLICATIONS

Fouladi et. al., Journal of Clinical Oncology, 2007, American Society of Clinical Oncology, vol. 25, No. 30, pp. 4806-4812.*
Stedman's Online Medical Dictionary, 2000, Lippincott Williams and Wilkins, 27th ed., p. 1.*
Hawkins et. al., Cancer, 2006, Wiley Interscience, vol. 106, pp. 1653-1663.*
O'Donnell et. al., Journal of Clinical Oncology, Apr. 2008, American Society of Clinical Oncology, vol. 26, No. 10, pp. 1588-1595.*
Leaf, Fortune, Mar. 2004, Time Inc., pp. 1-13.*
Choo et. al., Cancer Cell, 2006, Elsevier, vol. 9, iss. 2, pp. 77-79.*
Beger et al., World J. Surg., Societe Internationale de Chirugie, vol. 27, pp. 1075-1084 (2003).
Brown et al., "The Unique Physiology of Solid Tumors: Opportunities (and Problems) for Cancer Therapy", Cancer Res. 58, pp. 1408-1416 (1998).
Chabner at. al., Nature Reviews Cancer, Nature Publishing Group, vol. 5, pp. 65-72 (2005).
Choo et al., Cancer Cell, Elsevier, vol. 9, issue 2, pp. 77-79 (2006).
Freitas Jr. "Nanomedicine, vol. 1: Basic Capabilities" updated 2003, downloaded: www.nanomedicine.com/NMI/8.2.1.2, May 13, 2009, 4 pgs.
Guan et al., "Interventional treatments for hepatocellular carcinoma", Hepatobiliary Parcreat Dis. Int. 5, No. 4, pp. 495-500 (2006).
Jiang et al., "Role of mTOR in anticancer drug resistance: perspectives for improved drug treatment", Drug Resistance Updates, 11 (3), pp. 63-76 (2008).
Kato et. al., Cancer Chemother. Pharmacol., Springer-Verlag, vol. 37, pp. 289-296 (1996).
Kettenbach et al., "Drug-Loaded Microshperes for the Treatment of Liver Cancer: Review of Current Results", Cardiovasc. Int. Radiol 31, pp. 468-476 (2008).
Kuenen et al., Clinical Cancer Research, American Association for Cancer Research, vol. 9, pp. 1648-1655 (2003).
Liapi et al., "Transcatheter and Ablative Therapeutic Approaches for Solid Malignancies", J. of Clinical Oncology, 25, No. 8, pp. 978-986 (2007).
Mondesire, et al., "Targeting Mammalian Target of Rapamycin Synergistically Enhances Chemotherapy-Induced Cytotoxicity in Breast Cancer Cells", Clin. Cancer Res. 10: pp. 7031-7042 (2004).
Raoud "Natural History of Hepatocellular Carcinoma and Current Treatment Options", Sem. in Nucl. Med. 38, pp. S13-S18 (2008).
Rich et. al., Nature Rev. Drug Disc., Nature Publishing Group, vol. 3, pp. 430-446 (2004).
Ronnen et al., Invest. New Drugs, Springer, vol. 24, pp. 543-546 (2006).

(Continued)

*Primary Examiner* — Sarah Pihonak
(74) *Attorney, Agent, or Firm* — Squire Patton Boggs (US) LLP

(57) ABSTRACT

This invention is directed to methods of treating solid tumor cancers, particularly refractory cancers by administration of a drug capable of inhibiting mTOR and/or inhibiting an efflux pump and/or inhibiting HIF-1α and VEGF, the drug in particular being selected from the group consisting of sirolimus, everolimus, zotarolimus, tacrolimus, iolimus A9, deforolimus, AP23572, tacrolimus, temsirolimus, pimecrolimus, novolimus, 40-O-(3-hydroxypropyl), 40-O-[2-(2-hydroxy)ethoxy]ethyl-rapamycin and 40-O-tetrazolylrapamycin, the drug being administered along with a chemotherapeutic agent and/or radiation therapy.

20 Claims, No Drawings

(56) References Cited

OTHER PUBLICATIONS

Salazar et al., "Signle-Dose Half-Body Irradiation for Palliation of Multiple Bone Metastases from Solid Tumors", Cancer vol. 58, pp. 29-36 (1986).

Schabel, Jr. "The Use of Tumor Growth Kinetics in Planning "Curative" Chemotherapy of Advanced Solid Tumors", Cancer Res. 29, pp. 2384-2389 (1969).

Varela et al., "Chemoembolization of Hepatocellular Carcinoma With Drug Eluting Beads: Efficacy and doxorubicin pharmacokinetics", J. of Hepatology 46, pp. 474-481 (2007).

Berkland et al., "Fabrication of PLG microspheres with precisely controlled and monodisperse size distributions", J. of Contr. Release 73, pp. 59-74 (2001).

Lorenceau et al., "Generation of Polymerosomes from Double-Emulsions", Langmuir 21, pp. 9183-9186 (2005).

"Determination of Halofuginone Hydrobromide in Medical Animal Feeds", Analytical Methods Committee, Analyst. vol. 108, pp. 1252-1256 (1983).

Daniels, "Galenic principles of modern skin care products", Skin Care Forum, Issue 25, downloaded from www.scf-online.com/english/25_e/galenic Feb. 5, 2008, 16 pgs.

"Supercritical fluid", Sci-Tech. Dictionary, downloaded from www.answers.com/topic/supercritical-fluid?cat=technolony, Feb. 5, 2008, 3 pgs.

Berkland et al., "Fabrication of PLG microspheres with precisely controlled and monodisperse size distributions", J. of Controlled Release 73 pp. 59-74 (2001).

Bonegio et al., "Rapamycin Ameliorates Proteinuria-Associated Tubulointerstitial Inflammation and Fibrosis in Experimental Membranous Nephropathy", J. of Am. Soc. of Nephrology, 16, pp. 2063-2072 (2005).

Cao et al, "Inhibition of Mammalian Target of Rapamycin or Apoptotic Pathway induces Autphagy and Radiosensitizes PTEN Null Prostate Cancer Cells", Cancer Res 66, pp. 10040-10047 (2006).

Daniel et al., "Proinflammatory Effects in Experimental Mesangial Proliferative Glomerulonephritis of the Immunosuppressive Agent SDZ RAD, a Rapamycin Derivative", Exp. Nephrol 8, pp. 52-62 (2000).

DiJoseph et al., "The Effect of Rapamycin on Kidney Function in the Sprague-Dawley Rat", Transplantation vol. 53, No. 3 pp. 507-513 (1992).

Freitas, "Arteriovenous Microcirculation", Nanomedicine, vol. 1: Basic Capabilities, 4 pgs. (2003).

Gasparini et al., "Membrane Emulsification for Polyd, L-Lactide-Co-Glycolide Acid Microparticle Production: Influencing Factors", Abstract, Particle Formation and Crystallization Processess from Liquids, Slurries and Emulsions, the Preliminary program for 2007 Annual Meeting.

Giovanna et al., "Nanostructured Microspheres Produced by Supercritical Fluid Extraction of Emulsions", Biotechnology and Bioengineering vol. 10o, No. 5, Aug. 1, 2008. (Article Published Feb. 27, 2008).

Guertin et al., "An expanding role for mTOR in cancer", Trends in Molecular Medicine vol. 11, No. 8, 353-361 (2005).

Hu et al. "Nanoparticle Engineering Process for Enhancing the Dissolution Rates of Poorly Water Soluble Drugs", Drug Development and Industrial Pharmacy vol. 30, No. 3, pp. 233-245 (2004).

Hua et al., "Experimental and Numerical Studies of Droplet and Particle Formation in Electrohydrodynamic Atomization", Abstract, 1 pg. (2008).

Ishida et al., "A combinatorial approach to producing sterically stabilized (Stealth) immunoliposomal drugs", FEBS Letters 460, pp. 129-133 (1999).

Jian-Kang Chen et al., "Role of Mammalian Target of Rapamycin Signaling in Compensatory Renal Hypertrophy", J. of Am. Soc. of Nephrology, 16, pp. 1384-1391 (2005).

Kuang et al., "On the Fabrication of Microparticles Using Electrohydrodynamic Atomization Method", Molecular Engineering of Biological and Chemical Systems (MEBCS), 5 pgs. (2005).

Lloberas et al., "Mammalian Target of Rapamycin Pathway Blockade Slows Progression of Diabetic Kidney Disease in Rats", J. of Am. Soc. of Nephrology, 17, pp. 1395-1404 (2006).

Membrane Emulsification, Introduction, downloaded from www.chemsoc.org/ExemplarChem/entries2004/loughborough_cheng+woo/cheng+ Mar. 28, 2008, 1 pg.

Panchapakesan et al., "Drug Insight: thiazolidinediones and diabetic nephropathy-relevance to renoprotection", Nat. Clin. Pracice Nephrology vol. 1, No. 1 pp. 33-43 (2005).

Pautot et al., "Production of Unilamellar Vesicles Using an Inverted Emulsion", Langmuir 19, pp. 2870-2879 (2003).

Stallone et al., "Rapamycin for Treatment of Chronic Allograft Nephropathy in Renal Transplant Patients", J. of Am. Soc. of Nephrology, 16, pp. 3755-3762 (2005).

Tillier et al., "Determination of halofuginone in poultry feeds by high-performance liquid chromatography", J. of Chromatograpy 441, pp. 406-416 (1988).

Tumlin et al., "A Prospective, Open-Label Trial of Sirolimus in the Treatmen of Focal Segmental Glomerulosclerosis", Clin. J. Am. Soc. Nephtol. 1, pp. 109-116 (2006).

Vignot et al., "mTOR-targeted therapy of cancer with rapamycin derivatives", Annuals of Oncology 16: pp. 525-537 (2005).

Xu et al., "Pharmacogenomic profiling of the P13K/PTEN-AKT-mTOR pathway in common human tumors", Int. J. of Oncology 24, pp. 893-900 (2004).

* cited by examiner

METHOD OF TREATING MALIGNANT SOLID TUMORS

FIELD

This invention relates to medicine, cancer, chemotherapy, materials science and medical devices. In particular it relates to a method of treating solid tumors, especially those that are refractory to normal chemotherapy or radiation therapy.

BACKGROUND

Cancer is currently the second greatest cause of death in the United States behind coronary heart disease. Even though there is trend toward lower death rates from cancer in the U.S., it has been estimated that the annual personal and financial cost of cancer will be $1.62 trillion dollars by 2017. Further, according to the World Health Organization cancer is set to become the leading cause of death world-wide by 2010.

Cancer is an extremely elusive treatment target in that different types of cancer tend to display different biochemical characteristics and even within one type of cancer, the disease can evolve to become refractory to treatments that once were effective against that variety. This makes treatment choices difficult and is a prime reason for the large number of chemotherapeutics currently available to treat the disease as well as for the huge outlay of research dollars, at present approximately $6 billion dollars per year, spent in the effort to find new more efficacious drugs.

One of the more daunting problems is the ability of cancers to develop resistance to previously effective treatment regimes including both chemotherapeutic agents and radiation therapy. It has been postulated that among the causes of resistance several seem to be particularly ubiquitous across a broad spectrum of solid tumor cancers, those being the up-regulation of the Akt/mTOR pathway, which works to prevent chemotherapeutically induced apoptosis of cancer cells, the up-regulation of protein synthesis that can either directly inhibit the activity of a chemotherapeutic or that can develop an efflux pump to efficiently remove the chemotherapeutic from the cancerous cell before it has a chance to have any beneficial effect and activity of HIF-1α concurrent with the up-regulation of VEGF, which has the effect of stimulating angiogenesis and endothelial cell proliferation in the tumor.

What is needed is a means of inhibiting up-regulation of the Akt/mTOR pathway and/or the up-regulation of direct drug resistance or the development of efflux pump capability in the cancerous cells and/or inhibition of HIF-1α and VEGF. The current invention provides such a means.

SUMMARY

Thus, in one aspect the current invention is related to a method of treating a malignant solid tumor comprising identifying a malignant solid tumor in a patient; providing a plurality of microparticles comprising a drug capable of inhibiting the activity and/or the upregulation of mTOR, HIF-1α, VEGF and/or an efflux pump; delivering the particles through an artery to a point at or near the tumor; and administering a chemotherapeutic agent or radiation therapy.

In an aspect of this invention, the tumor is known or suspected to be refractory to the chemotherapeutic agent or to radiation therapy.

In an aspect of this invention, the drug is selected from the group consisting of sirolimus, everolimus, zotarolimus, tacrolimus, iolimus A9, deforolimus, AP23572, tacrolimus, temsirolimus, pimecrolimus, novolimus, 40-O-(3-hydroxypropyl), 40-O-[2-(2-hydroxy)ethoxy]ethyl-rapamycin and 40-O-tetrazolylrapamycin.

In an aspect of this invention, the drug is everolimus or zotarolimus.

In an aspect of this invention the drug is delivered at or near the tumor in a therapeutically effective bolus format.

In an aspect of this invention, the drug is delivered at or near the tumor in a therapeutically effective sustained release format.

In an aspect of this invention, the microparticles have a narrow mean particle size distribution around a selected mean particle size.

In an aspect of this invention, the mean particle size is 8 to 15 microns.

In an aspect of this invention, the mean particle size is about 12 to 13 microns.

In an aspect of this invention, the microparticles comprise solid polymeric particles.

In an aspect of this invention, the microparticles comprise liposomes.

In an aspect of this invention, the microparticles comprise polymersomes.

In an aspect of this invention, delivering the microparticles to or near the tumor comprises using a catheter.

In an aspect of this invention, delivering the microparticle to or near the tumor comprises injection into an artery at or near the tumor.

In an aspect of this invention, delivering the microparticles to or near the tumor comprises injecting the microparticles directly into the tumor.

In an aspect of this invention, administering the chemotherapeutic agent comprises local administration.

In an aspect of this invention, administering the chemotherapeutic agent comprises systemic administration.

DETAILED DESCRIPTION

In the present invention, a drug capable of inhibiting up-regulation of mTOR and/or inhibiting up-regulation of an efflux pump and/or inhibiting HIF-1α activity concurrent with up-regulation of VEGF activity is administered to a patient, preferably at or near a target solid tumor cancer along with administration of a chemotherapeutic agent and/or radiation therapy.

Among the drugs capable of effecting the above are, without limitation, sirolimus, everolimus, zotarolimus, tacrolimus, Biolimus A9, deforolimus, AP23572, tacrolimus, temsirolimus, pimecrolimus, novolimus, 40-O-(3-hydroxypropyl), 40-O-[2-(2-hydroxy)ethoxy]ethyl-rapamycin and 40-O-tetrazolylrapamycin.

It is understood that use of the singular throughout this application including the claims includes the plural and vice versa unless expressly stated otherwise. That is, "a" and "the" are to be construed as referring to one or more of whatever the word modifies. Non-limiting examples are: "a drug" which is understood to include one drug, two drugs or, under the right circumstances, as determined by those skilled in the treatment of diseased tissues, even more drugs serially or in combination unless it is expressly stated or is unambiguously obvious from the context that such is not intended. Likewise, "a biodegradable polymer" refers to a single polymer or a mixture of two or more polymers unless, again, it is expressly stated or absolutely obvious from the context that such is not intended.

As used herein, unless specified otherwise, any words of approximation such as without limitation, "about," "essentially," "substantially" and the like mean that the element so modified need not be exactly what is described but can vary from exact compliance with the written description by as much as ±15% without exceeding the scope of this invention.

The target tissue of this invention is malignant solid tumors. A solid tumor refers to an abnormal mass of tissue that usually does not contain cysts or liquid areas. A tumor that is not cancerous is described as "benign" while a cancerous tumor, the targets of this invention, are termed "malignant." Different types of solid tumors are named for the particular cells that form them, for example, sarcomas formed from connective tissue cells (bone cartilage, fat, etc.), carcinomas formed from epithelial tissue cells (breast, colon, pancreas, etc.) and lymphomas formed from lymphatic tissue cells (lymph nodes, spleen, thymus, etc.). Treatment of all types of solid tumors is within the scope of this invention.

A "refractory" solid tumor cancer, also referred to a "resistant cancer" is one that does not respond to treatment. The cancer may be resistant at the outset of treatment or it may develop resistance during treatment. While those tumors that are susceptible to treatment are of course within the scope of this invention, it is anticipated that it will be particularly useful in the treatment of refractory tumors.

As used herein, a "drug," a "therapeutic agent" or a "bioactive agent" all refer to the same thing and are used interchangeably: they refer to a material that has an effect on the biochemistry of a cancerous cell that sensitizes that cell to treatment with a chemotherapeutic agent or with radiation. The sensitization may be ab initio, that is sensitization of any solid tumor cell or it may be sensitization of cells that have become refractory to chemotherapy, i.e., treatment with a chemotherapeutic agent, or to radiation therapy. It is in this latter instance particularly, the treatment of refractory cancers, that this invention is particularly directed.

As used herein, "chemotherapeutic agent" refers to any substance that, when administered in a therapeutically effective amount to a patient suffering from a solid tumor cancer, has a therapeutic beneficial effect on the health and well-being of the patient. A therapeutic beneficial effect on the health and well-being of a patient includes, but it not limited to: (1) curing the cancer; (2) slowing the progress of the cancer; (3) causing the tumor to regress; or (4) alleviating one or more symptoms of the cancer. As used herein, a chemotherapeutic agent also includes any substance that, when administered in a prophylactic amount to a patient afflicted with a solid tumor cancer or who has been rendered substantially free of cancer as the result of one or more therapeutic treatment regimes, has a beneficial effect on the health and well-being of the patient. A prophylactic beneficial effect on the health and well-being of a patient includes, but is not limited to: (1) maintaining the cancer at a regressed level once such level has been achieved by a therapeutically effective amount of a substance, which may be the same as or different from the substance used in a prophylactic effective amount; or, (2) preventing or delaying recurrence of the cancer after a course of treatment with a therapeutically effective amount of a substance, which may be the same as or different from the substance used in a prophylactic effective amount, has concluded. In particular chemotherapeutic agent refers to those compounds known, or as by become known in the future, that have the ultimate effect of promoting apoptosis of cancerous cells leading to the ultimate demise of the solid tumor comprised of those cells.

A "therapeutically effective amount" refers to that amount of a therapeutic agent that will have a beneficial effect, which may be curative or palliative, on the health and well-being of the patient so afflicted. A therapeutically effective amount may be administered as a single bolus, as intermittent bolus charges, as short, medium or long term sustained release formulations or as any combination of these. As used herein, short-term sustained release refers to the administration of a therapeutically effective amount of a therapeutic agent over a period of about an hour to about 3 days. Medium-term sustained release refers to administration of a therapeutically effective amount of a therapeutic agent over a period of about 3 days to about 4 weeks and long-term refers to the delivery of a therapeutically effective amount over any period in excess of about 4 weeks, but in particular at present about 4 weeks to about a year.

As used herein, "radiation therapy" simply refers to any manner of treatment of solid tumor cancers with ionizing radiation as presently known or as may become known in the future and includes, without limitation, external beam radiotherapy, stereotatic radiotherapy, virtual simulation, 3-dimensional conformal radiotherapy, intensity-modulated radiotherapy, ionizing particle therapy and radioisotope therapy.

The particular type of release of a drug of this invention from its microparticulate carrier will depend in large part on the nature of the cancer treatment being employed. If a chemotherapy regime that requires multiple doses of the chemotherapeutic agent or agent over time, it may be preferential to use a sustained release format for the drug hereof so that it continues to affect the resistance of cancer cells between chemotherapeutic doses. On the other hand, if radiation therapy is contemplated, then a bolus or perhaps a short-term sustained release would be preferable. The manner of determining and fabricating particulate carriers exhibiting various release rates is known to those skilled in the art. These and any novel particulate carriers that are found to exhibit the desired release characteristics are within the scope of this invention.

As used herein, the use of "preferred," "preferably," or "more preferred," and the like refer to modify an aspect of the invention refers to preferences as they existed at the time of filing of the patent application.

Structural vehicles that may be used with the method of this invention include, without limitation, liposomes, polymersomes and solid microparticles of a mean size such that at least 80% of them will not be able to traverse the capillary system of a patient, in particular a human being.

As used herein, a "microparticle" refers to a solid having as its smallest cross-sectional, i.e., through the solid as opposed to along its surface, dimension about one micron. Presently preferred are microparticles having a mean size of about 10 to about 15 microns, still more preferably at present about 12.5 to about 13.5 microns. The solid can have any desired shape such as without limitation spherical, ellipsoid, rod-like, entirely random shaped, etc., although substantially spherical microparticles are well-known in the art, are readily prepared and are presently preferred. The microparticle may be constructed of one or more biocompatible substances and may be porous so as to permit elution of the therapeutic substance embedded in it or may be biodegradable such that as the particle degrades the therapeutic substance is released into the environment.

Particle size distributions may be represented in a number of ways, one of the most common of which is "mean particle size." A "mean" size may refer to a value based on particle length, width and/or diameter, on area or on volume. As used herein, "mean size" is determined by measuring the longest through-particle distance of each microparticle and then dividing by the total number of microparticles. Of course, this requires sophisticated equipment when dealing with the large numbers of microparticles contemplated by this invention but such equipment is well-known and readily available to those skilled in the art and such determination of mean size is commonplace in the art. To assure efficient capture of the microparticles of this invention at the capillary bed, not only should the microparticles have the stated mean size, the distribution of particle size should be a narrow as possible, that is as close to monodisperse as can be achieved. No specific size distribution is presently preferred because the narrower the better and, while several techniques are discussed below for achieving relatively narrow size distributions, as the state of the art advances, equipment and procedures for reaching even narrower size distributions will surely become available and all such equipment, procedures and size distributions will clearly be within the scope of this invention.

A particular method of determining mean particle size is dynamic light scattering ("DLS"), which is also called photon correlation spectroscopy, and which determines the hydrodynamic diameter or the Stokes diameter based on diffusion measurements. The hydrodynamic diameter includes solvent associated with the particle. This mean hydrodynamic diameter obtained from DLS is close to the volume-average diameter. One method is outlined in the International Standards Organization ("ISO") 13321. There are many other means of determining mean particle size known to those skilled in the art. Also known to those skilled artisans is the fact that the various means tend to give different results but the correlation of the results of one method to each other method is also well known. Thus, any method of particle size determination may be used but the result should be correlated with that obtained by DLS to assure a mean particle size that will be entrapped at the correct point in the circulatory system, i.e., the capillaries.

With regard to mean size and size distribution, as noted above, it is presently preferred that at least 80% of the microparticles administered into an artery serving a particular tissue are entrapped in the capillary system at the terminus of that artery. More preferably, at least 90% of the microparticles will be entrapped and most preferably at present, at least 99% of the microparticles will be entrapped.

The plurality of microparticles herein can comprise several different designs. In the simplest, the therapeutic agent is simply encapsulated in the carrier at a single concentration so that all microparticles are substantially the same with regard to drug load. In another design, the therapeutic agent can be encapsulated in the carrier, or if desired in several different carriers, at different concentrations in separate preparations and the microparticles formed in those separate preparations can be combined for administration to a patient. In yet another design, different therapeutic agents can be separately encapsulated in a carrier, or, again, in different carriers, at various concentrations, the microparticles being combined for administration or, if desired, administered sequentially. Two or more therapeutic agents can, of course, be encapsulated in the same microparticulate carrier such that the resulting microparticles each contain more than one therapeutic agent. Those skilled in the art will, based on the disclosure herein, be able to devise additional combinations of carrier and therapeutic agent(s); all such combinations are within the scope of this invention.

The selection of the presently preferred range of particle sizes is based on the average diameter of capillaries in the human body. A basic premise of this invention is that microparticles containing an appropriate therapeutic agent or combination of agents can be administered into an artery that directly services a tissue of interest. By "directly services" is meant that blood flowing through the artery proceeds in one direction only through the labyrinthine maze comprising artery→arterioles→metarterioles→capillaries→postcapillary venules→venules→vein. It is noted that the kidneys have a rather unique circulatory system: arteries→afferent→arterioles→glomerular→capillaries→efferent arterioles but the methods of this invention are eminently suitable for use with the kidneys as well as other organs. Thus, microparticles injected into blood in the artery have nowhere to go but into the diseased tissue where, depending on their size, they lodge in whichever of the preceding substructures has a diameter that is smaller than the selected particle mean size. It is noted that arterioles are generally regarded as having interior diameters in the range of approximately 10 to 50 microns, metarterioles about 10 to 20 microns and capillaries approximately 4 to 15 (average about 8) microns in diameter. Thus, microparticles having a mean size of about 10 to 15 micrometers should be efficiently trapped at the capillary level at least. For example, it has been reported that in one experiment 97% of 15 micrometer radiolabeled microspheres injected in an artery servicing the eye were entrapped at the first pass.

Entrapping the microparticles at the capillary level assures that the target diseased tissue receives the maximum benefit of the therapeutic agent encapsulated in the microparticles. This is due to the physiology of the capillary system. That is, the capillary system comprises a vast network of minute (averaging approximately 1 millimeter in length and 8 microns in diameter) vessels that permeates virtually every tissue in the mammalian body. As testament to the ubiquity of capillaries, it has been estimated that their number is approximately 19,000,000,000 and that most living tissue cells lie within 1-3 cell lengths of a capillary. Thus, to achieve maximum deployment of a therapeutic agent in a target tissue, it makes sense that the vehicle carrying the therapeutic agent be capable of maneuvering through the circulatory system to the capillary level. Administering the microspheres at the level of the arteriole or capillary also minimizes any potential embolic effect. As most cells lie within 1-3 cell lengths of multiple capillaries, when one capillary is embolized any ischemia created is confined to a very small zone of tissue. Cells in this zone can also received oxygen and nutrients from adjacent capillaries, which further prevents or minimizes ischemia. If larger microspheres are used, for example particles with a mean size greater than 20 microns, the zone of tissue embolized becomes proportionately greater. If cells at or near the center of this larger embolized region cannot be sufficiently perfused then frank necrosis may result.

As used herein, a "liposome" refers to a core-shell structure in which the shell comprises phospholipids or sphigolipids that surround a usually liquid, and in most cases aqueous, core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids. Any of the preceding techniques as well as any others known in the art or as may become known in the future may be used as compositions of therapeutic agents in or on a delivery interface of this invention. Liposomes comprising phospho- and/or sphingolipids may be used to deliver hydrophilic (water-soluble) or precipitated therapeutic compounds encapsulated within the inner liposomal volume and/or to deliver hydrophobic therapeutic agents dispersed within the hydrophobic core of the bilayer membrane.

In addition to solid microparticles and liposomes, a particle of this invention may be a polymersome, which is akin to a liposome wherein the shell is made up of synthetic amphiphilic polymers rather than phospholipids and sphigolipids. Examples of polymers that can be used to prepare polymersomes include, without limitation, poly(ethylene glycol)-b-poly(ε-caprolactone), poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates). Depending on the length and chemical nature of the polymers in the diblock copolymer, polymersomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate therapeutic agents by including the therapeutic agent in the water used to rehydrate the copolymer film. Polymersomes can also be force-loaded by osmotically driving the therapeutic agent into the core of the vesicle. Also as with liposomes, the loading efficiency is generally low. Recently, however, a technique has been reported that provides polymersomes of relative monodispersity and high loading efficiency; generation of polymersomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation. This technique along with any other technique know in the art or as may become known in the future can be used to prepare a composition of therapeutic agents for use in or on a delivery interface of this invention.

As used herein, "delivering" microparticles "at or near" a tumor refers to deposition of the particles in an artery sufficiently close to the target tumor to assure to the extent possible that the first instance of encountering a vessel of sufficiently small internal diameter to prevent passage of the particles will be the capillary system of the tumor itself. Such delivery can be accomplished by a number of means including, without limitation, the use of catheters and direct injection. Both of these methods of delivering microparticles to a specific locale in a patient's body are well-known to those skilled in the art and require no further explication here.

As mentioned previously, presently preferred delivery vehicles of this invention are microparticles, liposomes and polymersomes having a mean particle size such that the majority of the particles are entrapped in the capillary system of the target entity, here a solid tumor, upon the first pass of the plurality of particles through the patient's circulatory system.

As used herein, "first pass" refers to the first time a particle encounters the capillary bed at the terminus of a selected artery serving a diseased tissue. Microparticles that, for one reason or another, pass through the bed and find their way to venules and thence to veins will continue to circulate in the circulatory system until they once again encounter a capillary bed (although it may not be the capillary bed of the target tissue, which is why it is preferred that as high a percentage as possible are entrapped in the capillary bed of the target diseased tissue after having been administered into an artery serving that tissue). Again, for the purpose of this invention, it is preferred that at least 80% of the microparticles are entrapped at the first pass, more preferably 90% and presently most preferably, 99%.

As mentioned above, in order to achieve the preceding degrees of entrapment it is necessary to produce microparticles having a size distribution a narrow as possible around the target mean size wherein the target mean size is determined by the vessel size in the tissue being treated. That is, the mean particle size must be small enough to pass through an arteriole (afferent arteriole in the case of the kidneys) but large enough to be trapped by a capillary. While there may be other means to accomplish this and any such means is within the scope of this invention, presently preferred means include emulsification followed by supercritical fluid solvent extraction, ultrasonic atomization or droplet formation, electrohydrodynamic atomization and membrane emulsification.

Emulsification followed by supercritical fluid solvent extraction to form microparticles having a very narrow size range is a well-known technique in the art and therefore need not be extensively discussed herein, In brief, the technique involves the formation of an emulsion by dissolving a polymer and a therapeutic agent in a solvent for both, adding the solution under high shear to water containing emulsifying agent, sonicating to achieve a narrow droplet size range, passing the droplets through a porous membrane of well-defined pore size and then extracting the solvent from the microparticles using a supercritical fluid to give a hardened particle. A supercritical fluid, that is a fluid above its critical temperature and pressure, is used because of the physical properties of such fluids, which are intermediate between those of a gas those of a liquid. For example, supercritical carbon dioxide has a viscosity in the range of about 0.02 to about 0.1 centipoise (cP) whereas liquids have viscosities 0.5-1.0 cP and gasses have viscosities around 0.01 cP. Further, the diffusivities of solutes in supercritical carbon dioxide are up to a factor of 10 higher than in liquid solvents. This and the tunability of the solvating properties of supercritical fluids, which are a complex (but relatively well-understood) function of pressure and temperature, permit extremely selective extraction of one material, the solvent herein for instance, from others it may be combined with.

In any event, the hardened microparticles obtained after supercritical fluid solvent extraction may then be passed through yet another filter with well-defined pore size to still further control particle size distribution.

Atomization of a solution using an ultrasonic transducer can produce relatively monodisperse droplets. When captured in a appropriate bath and hardened, this can result in a narrow distribution of microspheres. The ultrasonic energy may be applied using a "horn" with the solution either flowing through it or being applied to its surface. The ultrasonic horn oscillates at a fixed frequency supplied by an ultrasonic transducer. Ultrasonic spray nozzles of this sort are readily available from Sono-Tek Corp, Milton, N.Y.

Another technique that produces relatively monodisperse particles involves the use of acoustic excitation of a liquid stream to break the stream up into monodisperse particles (Berkland, et al., J. Control. Rel., 2001, 73:59-74). The liquid stream is composed of a polymer and a therapeutic agent dissolved in one or more solvents. The droplets are carried by a carrier stream to a hardening bath where the solvent is removed. The frequencies needed to excite the liquid stream sufficiently to break it up into droplets are in the ultrasonic region of the spectrum.

Electrohydrodynamic atomization (EDHA) is another, relatively new but nevertheless well-characterized technique in the art for producing narrow size distribution, i.e. essentially monodisperse, microparticles. Again, without going into unnecessary detail since those skilled in the art will be very familiar with the technique, electrohydrodynamic atomization involves pumping a solution through a nozzle wherein a high voltage potential has been established between the tip of the nozzle and a counter-electrode. The high potential causes a build-up of electric charge in droplets at the nozzle tip and when the coulombic forces exceed the surface tension of the droplets, they separate, essentially explode, into smaller droplets. If parameters are optimized to achieve a stable spray, monodispersed droplets are obtained. Removal of solvent from the droplets yields monodisperse solid microparticles. Parameters that may be varied to achieve a particular average size droplet/particle include, without limitation, the applied voltage, the flow rate, density, conductivity and surface tension.

Normal emulsification techniques generally afford droplets of relative polydispersity, at least with regard to the narrow size distribution desired for use in the current invention. Thus, the requirement of one and perhaps two filtrations as set forth above with regard to emulsification/supercritical fluid solvent extraction. This is due primarily to the myriad parameters that come into play when preparing an emulsion such as, without limitation, the concentration of the agents, the nature of the drug/polymer/surfactant/solvent interaction, polymer molecular weight, sonication power, stir speed, fluid dynamics of the system and temperature. These shortcomings, at least with regard to the present invention, can be overcome by using the technique known as membrane emulsification.

Membrane emulsification is another relatively new technique for producing essentially monodisperse microparticles. As with standard emulsification followed by multiple filtrations and electrohydrodynamic atomization, membrane emulsification, while a relatively recent development, is well-known to those skilled in the art and need not be detailed herein. In brief, membrane emulsification involves the injection of an intended discontinuous phase through a porous membrane in which pore size is very carefully controlled into the intended continuous phase, which is moving past the porous membrane on the side opposite that from which the discontinuous phase is being injected. Droplets are sheared off the membrane by the moving continuous phase. Control of droplet size is quite exquisite compared to normal emulsification techniques because size is determined predominantly by easily varied parameters including the speed of the continuous phase, viscosity of the continuous phase, interfacial tension between the phases, the chemistry of the system—surfactant type and physical properties of all the constituents—and, of course, pore size. Newer techniques for creating porous membranes with a very precise pore size such as laser drilling and lithographic procedures have made membrane emulsification even more attractive as a technique for control of particle size distribution.

Polymeric microparticles presently preferred drug delivery vehicles of this invention. The polymer(s) must be biocompatible and can be either biostable or biodegradable. As used herein, biodegradable includes all means by which a polymer can be disposed of in a patient's body, which includes bioabsorption, resorption, etc. Biostable simply means that the polymer does not biodegrade or bioabsorb under physiological conditions over a relatively long period of time that may reach years.

As used herein, "biocompatible" refers to a polymer that both in its intact, that is, as synthesized, state and in its decomposed state, i.e., its degradation products, is not, or at least is minimally, toxic to living tissue; does not, or at least minimally and reparably, injure(s) living tissue; and/or does not, or at least minimally and/or controllably, cause(s) an immunological reaction in living tissue.

As used herein, "biodegradable" refers to any natural means by which a polymer can be disposed of in a patient's body. This includes such phenomena as, without limitation, biological decomposition, bioerosion, absorption, resorption, etc. Biodegradation of a polymer in vivo results from the action of one or more endogenous biological agents and/or conditions such as, without limitation, enzymes, microbes, cellular components, physiological pH and temperature and the like. Bioabsorbable or bioresorbable on the other hand generally refers to the situation wherein the polymer itself or its degradation products are removed from the body by cellular activity such as, without limitation, phagocytosis. Bioerodible refers to both physical processes such as, without limitation, dissolution and chemical processes such as, without limitation, backbone cleavage by hydrolysis of the bonds linking constitutional units of a polymer together. As used herein, biodegradable includes bioerodible, bioresobable and bioabsorbable.

Physiological conditions merely refers to the physical, chemical and biochemical milieu that constitutes the mammalian body and includes, without limitation, pH, temperature, enzymes and the presence of destructive cells such as phagocytes.

Among biocompatible, relatively biostable polymers useful as carriers for the preparation of microparticles of this invention are, without limitation, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins.

Biocompatible, biodegradable polymers that can be used for the carrier/particle-forming of this invention include, again without limitation, naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

Synthetic or semi-synthetic biocompatible, biodegradable polymers may also be used as carriers for the purpose of this invention. As used herein, a synthetic polymer refers to one that is created wholly in the laboratory while a semi-synthetic polymer refers to a naturally-occurring polymer than has been chemically modified in the laboratory. Examples of synthetic polymers include, without limitation, polyphosphazines, polyphosphoesters, polyphosphoester urethane, polyester urethanes, polyester urethane ureas, polyhydroxyacids, polyhydroxyalkanoates, polyanhydrides, polyesters, polyorthoesters, polyamino acids, polyoxymethylenes, poly(ester amides) and polyimides.

Further non-limiting examples of biocompatible biodegradable polymers that may be suitable as carriers herein include, without limitation, polycaprolactone, poly(L-lactide), poly(D,L-lactide), poly(D,L-lactide-co-PEG) block copolymers, poly(D,L-lactide-co-trimethylene carbonate), polyglycolide, poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, copoly(ether-esters) (e.g. PEO/PLA), polyalkylene oxalates, polyphosphazenes, PHA-PEG, and combinations thereof. The PHA may include poly (a-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly (4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly (anhydrides), poly(tyrosine carbonates) and derivatives thereof, poly(tyrosine ester) and derivatives thereof, poly (imino carbonates), poly(glycolic acid-co-trimethylene carbonate), polyphosphoester, polyphosphoester urethane, poly (amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly (sec-butyl methacrylate), poly(isobutyl methacrylate), poly (tert-butyl methacrylate), poly(n-propyl methacrylate), poly (isopropyl methacrylate), poly(ethyl methacrylate), poly (methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(etheresters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

Blends and copolymers of the above polymers may also be used and are within the scope of this invention. Based on the disclosures herein, those skilled in the art will recognize those implantable medical devices and those materials from which they may be fabricated that will be useful with the coatings of this invention.

As noted previously, a chemotherapeutic agent may be administered to a patient using the method of this invention in a bolus or sustained release format. The manner of fabrication of the carrier microparticle including the material of which it is made will determine how the chemotherapeutic agent is released after the particles have been delivered at or near the target tumor. Such fabrication techniques are well-documented in the patent and technical literature and need not be replicated here. Suffice it to say that any fabrication materials and procedures resulting in a desired release format is within the scope of this invention.

While the drug of this invention is delivered locally, that is, to or near the target tumor, the chemotherapeutic agent may be delivered and administered locally or systemically. Local delivery/administration refers to the initial deposition of the chemotherapeutic agent in the patient's body at, which includes directly into, or near the target tumor. Systemic delivery/administration refers to the introduction of the chemotherapeutic agent into the circulatory system at a location remote from the target tumor, the agent then traversing the circulatory system until a therapeutically effective portion of it encounters the tumor. If local delivery is desired, the chemotherapeutic agent may be included in the same microparticles carrying the drug of this invention or it may be contained in separate microparticles that have been fabricated of the same materials and in the configuration as the microparticles carrying the drug hereof or of entirely different materials and of an entirely different configuration depending on whether bolus or sustained delivery administration is desired. Those skilled in the art will be able, based on the disclosure herein, to determine the appropriate method of delivery/administration and fabricate microparticles accordingly.

As noted previously, the method of this invention can be used to treat any solid tumor cancer to which blood is supplied by a dedicated, relatively reachable artery such as the renal, hepatic, pulmonary and cardiac arteries. As such, the chemotherapeutic agent(s) which may be used in the instant method include virtually all known chemotherapeutics as well as those that become available in the future.

Likewise, any suitable manner of radiotherapy including, but not limited to, conventional external beam radiotherapy, stereotactic radiotherapy, virtual simulation, three-dimensional conformal radiotherapy, intensity modulated radiotherapy, particle or proton radiotherapy and radioisotope radiotherapy may be used with the method herein.

As used herein, a "patient" refers to any species that might benefit from treatment using the method herein but at present is preferably a mammal and most preferably a human being.

What is claimed:

1. A method of delivering a drug to a malignant solid tumor comprising:
    delivering a plurality of microparticles comprising a drug capable of inhibiting the activity and/or the upregulation of mTOR through an artery to a point at or near the tumor, wherein:
        the microparticles have a mean particle size that is small enough to pass through a metarteriole having an interior diameter of about 10 to 20 microns but large enough to be trapped by a capillary having an interior diameter of approximately 4 to 15 microns, and
        at least 80% of the microparticles administered into the artery are entrapped in a capillary system at a terminus of the artery; and
    subsequently administering a chemotherapeutic agent or radiation therapy.

2. The method of claim 1, wherein the tumor is known or suspected to be refractory to the chemotherapeutic agent or the radiation therapy.

3. The method of claim 1, wherein the drug is selected from the group consisting of sirolimus, everolimus, zotarolimus, tacrolimus, Biolimus A9, deforolimus, AP23572, temsirolimus, pimecrolimus, novolimus, 40-O-(3-hydroxypropyl), 40-O-[2-(2-hydroxyl)ethoxy]ethyl-rapamycin and 40-O-tetrazolylrapamycin.

4. The method of claim 1, where the drug is everolimus or zotarolimus.

5. The method of claim 1, wherein the drug is delivered at or near the tumor in a therapeutically effective bolus format.

6. The method of claim 1, wherein the drug is delivered at or near the tumor in a therapeutically effective sustained release format.

7. The method of claim 1, wherein the microparticles have a mean particle size of 8 to 15 microns.

8. The method of claim 7, wherein the mean particle size is about 12 to 13 microns.

9. The method of claim 1, wherein the microparticles comprise solid polymeric particles.

10. The method of claim 1, wherein the microparticles comprise liposomes.

11. The method of claim 1, wherein the microparticles comprise polymersomes.

12. The method of claim 1, wherein delivering the microparticles to or near the tumor comprises using a catheter.

13. The method of claim 1, wherein delivering the microparticles to or near the tumor comprises injection into an artery at or near the tumor.

14. The method of claim 1, wherein delivering the microparticles to or near the tumor comprises injecting the microparticles directly into the tumor.

15. The method of claim 1, wherein administering the chemotherapeutic agent comprises local administration.

16. The method of claim 1, wherein administering the chemotherapeutic agent comprises systemic administration.

17. The method of claim 1, wherein the artery is selected from a hepatic artery, a renal artery, a pulmonary artery, and a cardiac artery.

18. The method of claim 1, wherein at least 90% of the microparticles administered into the artery are entrapped in the capillary system at the terminus of the artery.

19. The method of claim 1, wherein at least 99% of the microparticles administered into the artery are entrapped in the capillary system at the terminus of the artery.

20. The method of claim 1, wherein the capillaries in the capillary system have an average diameter of about 8 microns.

* * * * *